United States Patent [19]
Mineta et al.

[11] Patent Number: 5,976,409
[45] Date of Patent: Nov. 2, 1999

[54] SWALLOW-TAIL-SHAPED LIQUID CRYSTAL COMPOUND

[75] Inventors: Hiroshi Mineta; Masahiro Johno; Tomoyuki Yui; Takahiro Matsumoto, all of Tsukuba, Japan

[73] Assignee: Mitsubishi Gas Chemical Company, Inc., Tokyo, Japan

[21] Appl. No.: 09/099,772

[22] Filed: Jun. 19, 1998

[30] Foreign Application Priority Data

| Jun. 20, 1997 | [JP] | Japan | 9-164286 |
| Aug. 6, 1997 | [JP] | Japan | 9-211884 |
| Oct. 9, 1997 | [JP] | Japan | 9-277316 |
| Oct. 9, 1997 | [JP] | Japan | 9-277317 |

[51] Int. Cl.$^6$ ............................ C09K 19/12; C07C 69/76
[52] U.S. Cl. ..................... 252/299.65; 560/65; 560/102
[58] Field of Search ...................... 252/299.65; 560/65, 560/102

[56] References Cited

U.S. PATENT DOCUMENTS

| 4,943,386 | 7/1990 | Takehara et al. | 252/299.65 |
| 5,098,602 | 3/1992 | Hirai et al. | 252/299.65 |
| 5,374,375 | 12/1994 | Yui et al. | 252/299.65 |
| 5,424,005 | 6/1995 | Suzuki et al. | 252/299.65 |

(List continued on next page.)

FOREIGN PATENT DOCUMENTS

| 1213390 | 8/1989 | Japan . |
| 1316339 | 12/1989 | Japan . |
| 1316367 | 12/1989 | Japan . |
| 1316372 | 12/1989 | Japan . |
| 2-28128 | 1/1990 | Japan . |

OTHER PUBLICATIONS

Chandani, et al, "Tristable Switching in Surface Stabilized Ferroelectric Liquid Crystals with a Large Spontaneous Polarization", Japanese Journal of Applied Physics, vol. 27, No. 5, pp. L729–L732 (May 1988).

Chandani, et al, "Novel Phases Exhibiting Tristable Switching", Japanese Journal of Applied Physics, vol. 28, No. 7, pp. L1261–L1264 (Jul. 1989).

Chandani, et al, "Antiferroelectric Chiral Smectic Phases Responsible for the Tristable Switching in MHPOBC", Japanese Journal of Applied Physics, vol. 28, No. 7, pp. L1265–L1268 (Jul. 1989).

Johno, et al, "Smectic Layer Switching by an Electric Field in Ferro–electric Liquid Crystal Cells", Japanese Journal of Applied Physics, vol. 28, No. 1, pp. L119–L120 (Jan. 1989).

(List continued on next page.)

*Primary Examiner*—C. H. Kelly
*Attorney, Agent, or Firm*—Sherman and Shalloway

[57] ABSTRACT

A swallow-tail-shaped liquid crystal compound of the following general formula (1),

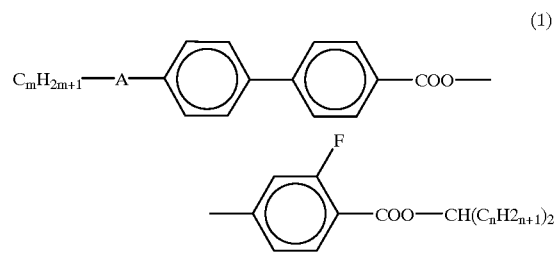

wherein A is —O—, —COO— or a single bond (—), m is an integer of 4 to 12, and n is an integer of 2 to 4.

The above swallow-tail-shaped liquid crystal compound of the present invention is a novel achiral anti-ferroelectric liquid crystal and can be converted to an optically active anti-ferroelectric liquid crystal by mixing it with an optically active compound as a chiral dopant.

4 Claims, 2 Drawing Sheets

Vex: Driving voltage applied to device
Vc: Voltage generated between the upper and lower surfaces of an insulation layer by charge of a polarization inversion current
Veff: Effective voltage actually applied to liquid crystal
P: Polarization of liquid crystal
ip: Polarization inversion current
S: Electrode area of liquid crystal device
d': Thickness of insulation layer
ε': Dielectric constant of insulation layer

U.S. PATENT DOCUMENTS

| | | | |
|---|---|---|---|
| 5,534,190 | 7/1996 | Johno et al. | 252/299.65 |
| 5,705,094 | 1/1998 | Takeuichi et al. | 252/299.01 |
| 5,716,544 | 2/1998 | Motoyama et al. | 252/299.65 |
| 5,820,786 | 10/1998 | Sage et al. | 252/299.66 |
| 5,840,209 | 11/1998 | Mineta et al. | 252/299.67 |
| 5,861,109 | 1/1999 | Goodby et al. | 252/299.65 |

OTHER PUBLICATIONS

Johno, et al, "Correspondence Between Smectic Layer Switching and DC Hysteresis of Apparent Tilt Angle in an Antiferroelectric Liquid Crystal Mixture", Japanese Journal of Applied Physics, vol. 29, No. 1, pp. L111–L114 (Jan. 1990).

Suzuki, et al, "New Fluorine–Containing Ferroelectric Liquid Crystal Compounds Showing Tristable Switching", Liquid Crystals, 1989, vol. 6, No. 2, pp. 167–174.

FIG. 1

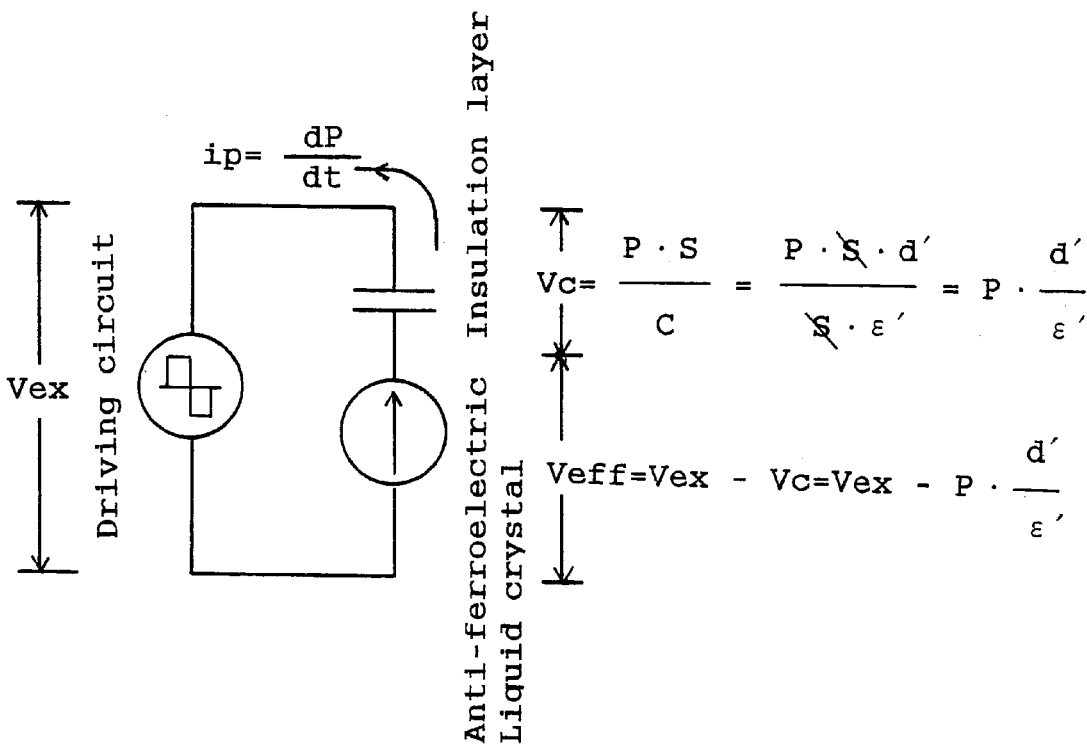

Vex: Driving voltage applied to device

Vc: Voltage generated between the upper and lower surfaces of an insulation layer by charge of a polarization inversion current Veff: Effective voltage actually applied to liquid crystal P: Polarization of liquid crystal ip: Polarization inversion current S: Electrode area of liquid crystal device d': Thickness of insulation layer ε': Dielectric constant of insulation layer $E_{eff} = \dfrac{V_{eff}}{d}$ $E_{eff}$: Electric field intensity actually applied to liquid crystal d: Thickness of liquid crystal layer $C_i$ (i=1-4): Threshold in device having no insulation layer Insulation layer factor: $\alpha = \dfrac{d'}{\varepsilon'} \cdot \dfrac{1}{d}$ Apparent electric field intensity:

$$E_{ex} = \dfrac{V_{ex}}{d} = E_{eff} + \alpha \cdot P$$

SWALLOW-TAIL-SHAPED LIQUID CRYSTAL COMPOUND

TECHNICAL FIELD OF THE INVENTION

The present invention relates to a novel liquid crystal compound having an achiral anti-ferroelectric phase.

PRIOR ART

A liquid crystal display device has so far been used mainly to a variety of small-sized display devices on account of its low-voltage operation, low-power consumption and display capability with a thin screen. Further, with the recent application and increased use of a liquid crystal display device to/in the fields of information, office automation-related machines and equipment, and television sets, demands are rapidly increasing for high-performance and large-sized liquid crystal display devices having a larger display capacity and a higher display quality than those of a conventional CRT display device.

However, as long as a nematic liquid crystal compound available at present is used in a display device, even with an active matrix driven liquid crystal display device (TFT) used in a liquid crystal television set, it is not easy to increase its size and decrease its production cost due to its complicated production process and a low yield. In a simple matrix driven STN liquid crystal display device (STN), the driving of a large display capacity is not necessarily easy and its response time is also limited, so that the display of video frames at a high duty ratio is therefore difficult. Consequently, it is difficult to say at present that a nematic liquid crystal display device can satisfy demands for the above high-performance and large-sized liquid crystal display device.

Further, both TFT and STN display devices using a nematic liquid crystal compound have a serious problem with regard to their narrow viewing angle. Although a variety of solutions are proposed, it is difficult to find out a radical solution as long as a nematic liquid crystal compound is used.

Under the circumstances, a liquid crystal display device for which a ferroelectric liquid crystal is used has been attracting attention as a liquid crystal display device with a high response and a wide viewing angle. A surface-stabilized ferroelectric liquid crystal (SSFLC) device disclosed by Clark and Lagerwall has been attracting attention in that it has a fast response and a wide viewing angle which have not been achieved in the past. Its switching characteristics have been studied in detail, and a number of ferroelectric liquid crystal compounds have been synthesized for optimizing various physical property constants. When a ferroelectric liquid crystal compound is used for a liquid crystal display device, however, a special devising is required with regard to the alignment of a liquid crystal for obtaining a practically acceptable contrast due to its insufficient threshold characteristic and chevron-structured layer. Further, the alignment control of liquid crystal molecules is so difficult that it is not easy to accomplish the bistability, which is one of the greatest characteristics of SSFLC, with high reproducibility. Further, it is difficult to restore the alignment destroyed by a mechanical shock. It is therefore essential to overcome the above problems for its practical use.

As described above, various efforts including the development of a new mode have been made for attaining a larger-sized and higher-resolution liquid crystal device. Under the circumstances, however, developments of devices having switching mechanisms totally different from that of SSFLC are also under way. For example, switching among tristable states of a liquid crystal compound having an anti-ferroelectric phase (to be referred to as "anti-ferroelectric liquid crystal compound" hereinafter) is one of these new switching mechanisms (Japanese Journal of Applied Physics, Vol. 27, pp. L729, (1988)).

A liquid crystal display device using an anti-ferroelectric liquid crystal compound has three stable states, i.e., two uniform states (Ur, Ul) observed in a ferroelectric liquid crystal device and a third state. Chandani et al report that the above third state is an anti-ferroelectric phase (Japanese Journal of Applied Physics, Vol. 28, pp. L1261, (1989), Japanese Journal of Applied Physics, Vol. 28, pp. L1265, (1989)).

The above switching among tristable states is the first characteristic of an anti-ferroelectric liquid crystal device.

The second characteristic of the anti-ferroelectric liquid crystal device is that a sharp threshold voltage exists with respect to an applied voltage. Further, the anti-ferroelectric liquid crystal device has a memory effect, which is the third characteristic of the anti-ferroelectric liquid crystal device.

The above excellent characteristics serve to accomplish a liquid crystal display device having a fast response and a good contrast.

The anti-ferroelectric liquid crystal has another great characteristic in that its layer structure easily performs switching when an electric field is applied (Japanese Journal of Applied Physics, Vol. 28, pp. L119, (1989), Japanese Journal of Applied Physics, Vol. 29, pp. L111, (1990)).

The above characteristics permit the production of a liquid crystal display device free of defects and capable of self-restoring an alignment, and a liquid crystal device having an excellent contrast can be attained.

As an anti-ferroelectric liquid crystal compound, there are known compounds disclosed in JP-A-1-213390, JP-A-1-316339, JP-A-1-316367, JP-A-1-316372, JP-A-2-28128 and "Liquid Crystals", Vol. 6, pp. 167 (1989). The number of anti-ferroelectric liquid crystal compounds which have been so far known is not so large as that of ferroelectric liquid crystal compounds, while anti-ferroelectric liquid crystal compounds are increasing in number with the development in their studies.

On the other hand, as a progress has been made in the development of a liquid crystal display device using an anti-ferroelectric liquid crystal compound, there have been revealed defects unique to an anti-ferroelectric liquid crystal.

One of the defects is large spontaneous polarization. That is, there occurs a problem which will be discussed below when the spontaneous polarization is large.

Practically, it is preferable that an anti-ferroelectric liquid crystal is a material which gives a high steepness of optical transmittance change against applied voltage when adapted to a liquid crystal display device. Further, it has been experimentally recognized that the steepness of the liquid crystal display device is greatly related to the thickness of each of an insulation layer and an alignment layer.

It has been studied what factors can help explain the above phenomenon. In this studies, both an insulation layer and an alignment layer together will be referred to as "alignment layer".

BRIEF DESCRIPTION OF DRAWINGS

FIG. 1 shows an equivalent circuit of an anti-ferroelectric liquid crystal device.

Figure 2:
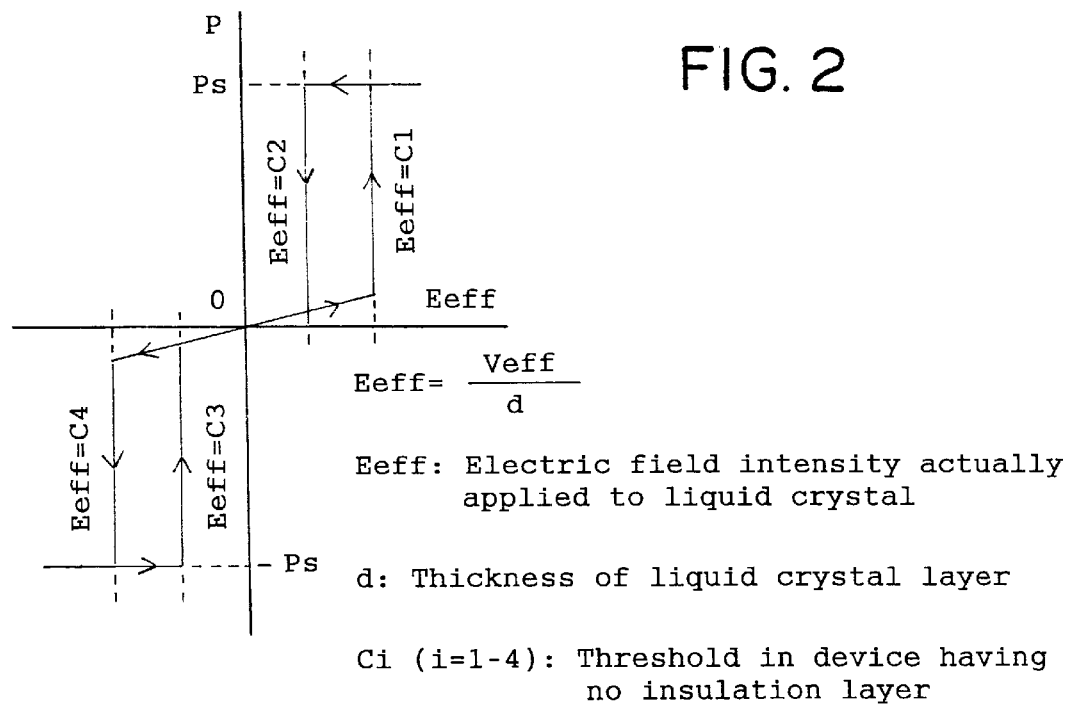
FIG. 2 shows a simulation result on the steepness of threshold when alignment layer is absent.

The symbols used in each of the drawings represent the following.

Vex: Driving voltage applied to device.

Vc: Voltage generated between an upper surface and a lower surface of an insulation layer when polarization inverting current is charged.

Veff: Effective voltage actually applied to liquid crystal.

P: Polarization of liquid crystal ip: Polarization inverting current

S: Electrode area of liquid crystal device d': Thickness of insulation layer $\epsilon'$: Dielectric constant of insulation layer Eeff: Intensity of electric field actually applied to liquid crystal d: Thickness of liquid crystal layer Ci(i=1–4): Threshold voltage in device having no insulation layer $\alpha$: Insulation layer factor Eex: Apparent electric field intensity The equivalent circuit of an anti-ferroelectric liquid crystal display device will be explained first with reference to FIG. 1.

FIG. 1 shows an equivalent circuit which comprises an anti-ferroelectric liquid crystal which is an electric current source to generate a polarization current depending on an applied voltage, an alignment layer which is an electrostatic capacitor C to be connected to the liquid crystal in series, and a driving circuit that is an ideal voltage source.

In FIG. 1, Vex is a driving voltage applied to a device, Vc is a voltage generated between the upper and lower surfaces of an alignment layer by the charge of a polarization inverting current, Veff is an effective voltage to be actually applied to the liquid crystal, P is a spontaneous polarization of the liquid crystal, S is an electrode area of the liquid crystal device, d' is a thickness of the insulation(alignment) layer, and $\epsilon'$ is a dielectric constant of the insulation (alignment) layer.

Vc is calculated according to the following equation (1).

$$Vc = PS/C = PSd'/(S\epsilon') = P(d'/\epsilon') \quad (1)$$

On the basis of the above equation, Veff is expressed by the following equation (2).

$$Veff = Vex - Vc = Vex - P(d'/\epsilon') \quad (2)$$

As shown in the equation (2), the voltage actually applied to the liquid crystal is lower than the externally applied voltage by a product of the polarization P of the liquid crystal, the thickness d' of the alignment layer and a reciprocal number $1/\epsilon'$ of the dielectric constant of the alignment layer.

Then, when a thickness of the liquid crystal layer filled in a liquid crystal cell is taken as d, an electric field Eeff actually applied to the liquid crystal is expressed by the following equation (3).

$$Eeff = Veff/d \quad (3)$$

An apparent electric field intensity Eex is expressed by the following equation (4).

$$Eex = Vex/d = (Veff + Vc)/d = Veff/d + P(d'/\epsilon')/d = Eeff + \alpha \quad (4)$$

wherein $$\alpha = d'/(\epsilon' d) \quad (5)$$

An anti-ferroelectric liquid crystal shows a hysteresis in optical response to a charged voltage, and four threshold voltages are thinkable with regard to the hysteresis.

When no alignment layer is present, the second term in the equation (4) is 0, and hence Eex=Eeff. Each threshold is Eeff (=Eex), and in this case, these thresholds do not incline to an electric field. FIG. 2 shows this appearance.

When an alignment layer is present, the equation (4) is modified to obtain the following equation (6).

$$Eeff = Eex - \alpha P \quad (6)$$

Figure 3:
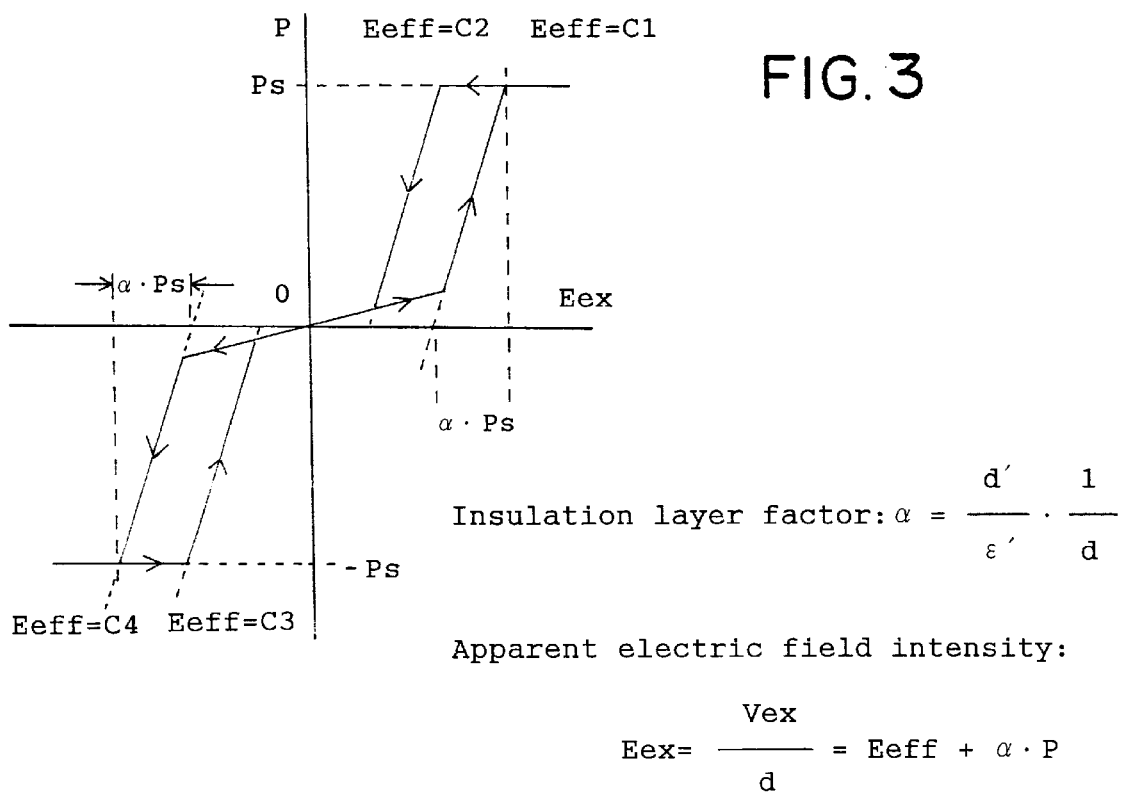
FIG. 3 shows a simulation result on the steepness of threshold when an alignment layer is present.

That is, an effective electric field exerting on the liquid crystal is lower than the applied electric field Eex by $\alpha \cdot P$. As a result, the hysteresis is strained to a great extent due to the contribution of the $\alpha \cdot P$ as shown in FIG. 3.

The above studies show that the strain of hysteresis is greatly caused by the interaction of the spontaneous polarization and the alignment layer. For obtaining a liquid crystal device having the strain of hysteresis reduced, therefore, it is effective to decrease the above interaction so as to make it as small as possible.

For the above purpose, the measures that can be specifically taken include the use of an alignment layer having a high dielectric constant, the decreasing of the thickness of the alignment layer and the decreasing of the spontaneous polarization of the liquid crystal, as is clear from the above equations (5) and (6). In the above measures, it is very difficult to select an alignment layer having a high dielectric constant, since few kind of materials having a high dielectric constant are available for industrial use. The measures that can be specifically taken is therefore to decrease the thickness of the alignment layer and to decrease the spontaneous polarization of the liquid crystal.

Generally, an anti-ferroelectric liquid crystal compound has a considerably large spontaneous polarization, and a liquid crystal compound having relatively excellent physical properties has a spontaneous polarization of 200 nc/cm$^2$ or more. Therefore, unless the thickness of the alignment layer is much decreased, the strain of the hysteresis is considerably large. However, when the thickness of the alignment layer is decreased, there occurs a problem that the alignment state of the liquid crystal molecules is too defective to secure a contrast.

The measure for correcting the strain of the hysteresis by decreasing the thickness of the alignment layer is therefore considerably limited, and it is very difficult to use the above measure for practical solution.

On the other hand, there is employed a method in which the spontaneous polarization of a liquid crystal compound is decreased by incorporating a proper compound having no spontaneous polarization into the liquid crystal compound, that is, by diluting the liquid crystal compound to decrease its concentration. Since, however, the response speed of a liquid crystal is determined by a product of an applied voltage and a spontaneous polarization, there occurs another new problem that the response speed decreases when the spontaneous polarization is simply decreased by dilution.

Under the circumstances, for obtaining a device having a decreased strain of hysteresis, attempts have been so far made to develop an anti-ferroelectric liquid crystal compound having a low spontaneous polarization, a low threshold voltage and a low viscosity, but it is a current situation that no satisfactory achievements have been obtained.

On the other hand, if the method of developing a liquid crystal material by combining a chiral dopant with a host liquid crystal, which method was successful in the development of a ferroelectric liquid crystal display device, can be applied to the development of an anti-ferroelectric liquid crystal material as well, there can be developed a high-response material which has a low spontaneous polarization and has a low viscosity.

No achiral anti-ferroelectric liquid crystal was found in the past, but in recent years, an achiral anti-ferroelectric liquid crystal phase has been found in the following compounds.

(1) $C_9H_{19}$—O—Ph—C≡C—COO—Ph—Ph—COO—CH$(C_3H_7)_2$

I(70)SA(55)SCA'(40)Cr

Nishiyama et al., J. MATER.CHEM., 1992, 2(10), 1015

(2) $C_8H_{17}$—O—Ph—Ph—COO—Ph—COO—CH$(C_6H_{13})_2$

I(81)SA(61.9)SCA'(?)Cr, Melting point: 69.7° C.

(3) $C_8H_{17}$—O—Ph—Ph—COO—Ph—COO—CH$(C_3H_7)_2$

I(119.7)SA(103.2)SCA'(?)Cr, Melting point 80.0° C.

Y. Ouchi et al., J. MATER.CHEM., 1995, 5(12), 2297

(4) $C_8H_{17}$—O—Ph—Ph—COO—Ph(2F)—COO—CH$(C_nH_{2n+1})_2$ n=2; I(108.6)SA(82.2)SCA'(32)Cr n=3; I(72.9)SA(56.8)SCA'(40)Cr n=4; I(58.1)SA(45.7)SCA'(40)Cr

C. J. Booth et al., Liquid Crystals, 1996, 20(4), 387

In the above formulae, —Ph— is a 1,4-phenylene group and —Ph(2F)— is a 1,4-phenylene group having a fluorine atom on the 2-position. In the above phase sequences, parenthesized value shows a phase transition temperature (° C.), I is an isotropic phase, SA is a smectic A phase, SCA' is an achiral anti-ferroelectric phase, and Cr is a crystal phase.

The number of achiral anti-ferroelectric liquid crystals which have been so far found is very small as described above. In terms of chemical structure, it seems that compounds which have an alkyl group having a swallow-tail-shaped branched terminals in place of an optically active group of a chiral anti-ferroelectric liquid crystal exhibit an achiral anti-ferroelectric phase. On the other hand, as is clear from the above phase sequences, in view of practical use, those achiral anti-ferroelectric liquid crystal compounds which have been so far found have problems that the upper-limit temperature of their anti-ferroelectric phase is low and that the temperature range of their anti-ferroelectric phase is narrow, so that it is problematic to use them as a host liquid crystal.

The present invention has been invented from the above points of view, and has been completed by finding that a biphenyl-phenyl ester liquid crystal having a swallow-tail-shaped terminal group and containing a fluorine atom on the 3-position of a phenyl group is an achiral anti-ferroelectric liquid crystal compound which has an achiral anti-ferroelectric phase in a broad temperature range and whose achiral anti-ferroelectric phase has a high upper-limit temperature.

Means to solve the Invention

That is, according to the present invention, there is provided a swallow-tail-shaped liquid crystal compound of the following general formula (1),

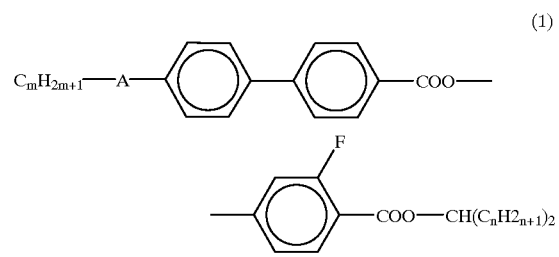

wherein A is —O—, —COO— or a single bond (—O, m is an integer of 4 to 12, and n is an integer of 2 to 4.

In the compound of the above general formula (1), A is —O—, —COO— or a single bond, and of these, A is preferably —O—. m is an integer of 4 to 12, and there can be provided a liquid crystal compound which is more preferable in that its achiral anti-ferroelectric phase shows a high upper-limit temperature and has a broad temperature range when m is 6 to 10. n is an integer of 2 to 4, and the achiral anti-ferroelectric phase has a broad temperature range and shows a high upper-limit temperature when n is 2 or 3. In view of practical use, it is preferred that the temperature range of the anti-ferroelectric phase includes room temperature and that the upper-limit temperature of the anti-ferroelectric phase is 50° C. or higher.

Effect of the Invention

The present invention can provide a novel achiral anti-ferroelectric liquid crystal compound. The novel achiral anti-ferroelectric liquid crystal compound provided by the present invention can be converted to an optically active anti-ferroelectric liquid crystal by mixing it with an optically active compound as a chiral dopant.

EXAMPLES

The present invention will be explained in more detail with reference to the following Examples and Comparative Examples, while the present invention shall not be limited thereto.

Example 1 (Formula (1): A=—O—, m=9, n=2 (E1))

Preparation of 3-fluoro-4-(1-ethylpropyloxycarbonyl)phenyl=4'-n-nonyloxybiphenyl-4-carboxylate (1) Preparation of 4-(4'-n-nonyloxy)biphenylcarboxylic acid 10.0 Grams of 4-(4'-hydroxy)biphenylcarboxylic acid and 17.3 g of n-nonyl bromide were added to a mixture comprising 1,500 ml(milliliter) of ethanol and 200 ml of water, and the mixture was allowed to react under reflux for 10 hours. Thereafter, 500 ml of water was added, and the mixture was stirred for 3 hours.

After the completion of the reaction, concentrated hydrochloric acid was added to acidify the reaction mixture, then, 500 ml of a solvent was distilled off, and the remainder of the mixture was cooled to room temperature to give a white solid. The white solid was fully washed with water and then recrystallized from chloroform to give 12.8 g of an end product in the form of a white crystal.

(2) Preparation of 4-acetoxy-2-fluorobenzoic acid 4.3 Grams of 2-fluoro-4-hydroxybenzoic acid and 8.4 g of acetic acid anhydride were placed in a two-necked flask and mixed therein. While the mixture was being cooled with water, five drops of sulfuric acid were added. After the termination of heat generation, the mixture was heated at 80° C. for 30 minutes.

Then, the reaction mixture was poured into a cold water to precipitate a crystal, which was then subjected to filtration. The crystal was dried under vacuum and used in a subsequent step. The yield of the end product was 4.7 g.

(3) Preparation of 4-acetoxy-2-fluoro-1-(1-ethylpropyloxycarbonyl)benzene 1.0 Gram of 4-acetoxy-2-fluorobenzoic acid was added to 7 ml of thionyl chloride, and the mixture was allowed to react under reflux for 5 hours. Thereafter, excessive thionyl chloride was distilled off, and a mixture comprising 1 ml of pyridine, 4 ml of dry ether and 0.6 g of 3-pentanol was added dropwise to the above mixture. After the addition, the resulting mixture was stirred at room temperature for one day and diluted with 200 ml of ether, and an organic layer was washed consecutively with diluted hydrochloric acid, a 1N sodium hydroxide aqueous solution and water, and dried over magnesium sulfate.

The solvent was distilled off, and the resultant crude product was purified by silica gel column chromatography using hexane/ethyl acetate as a solvent, to give 0.7 g of the end product.

(4) Preparation of 4-hydroxy-2-fluoro-1-(1-ethylpropyloxycarbonyl)benzene 0.5 Gram of the compound obtained in the above (3) was dissolved in 30 ml of ethanol, and 1.5 g of benzylamine was added dropwise thereto. Further, the mixture was stirred at room temperature for one day and diluted with 300 ml of ether, and the diluted mixture was washed with diluted hydrochloric acid and then with water and dried over magnesium sulfate.

The solvent was distilled off, and silica gel column chromatography was used for purification to give 0.3 g of the end product.

(5) Preparation of 3-fluoro-4-(1-ethylpropyloxycarbonyl)phenyl=4'-n-nonyloxybiphenyl-4-carboxylate To 0.5 g of the compound obtained in the above (1) was added 10 ml of thionyl chloride, and the mixture was refluxed under heating for 10 hours. Thereafter, excessive thionyl chloride was distilled off, and 10 ml of pyridine and 25 ml of toluene were added to the remaining of the mixture. Then, a solution of 0.3 g of the compound obtained in the above (4) in 25 ml of benzene solution was added dropwise thereto, and the resulting mixture was allowed to react at room temperature for 10 hours.

After the completion of the reaction, the reaction mixture was diluted with 300 ml of ether, and the diluted mixture was washed consecutively with diluted hydrochloric acid, a 1N sodium carbonate aqueous solution and water. An organic layer was dried over magnesium sulfate.

Thereafter, the solvent was distilled off, and silica gel column chromatography was used for isolation. Finally, an isolated product was recrystalllized from ethanol to give 0.1 g of the end product.

Example 2 (Formula (1): A=—O—, m=9, n=3 (E2))

Preparation of 3-fluoro-4-(1-propylbutyloxycarbonyl)phenyl=4'-n-nonyloxybiphenyl-4-carboxylate Example-3 (Formula (1): A=—O—, m=9, n=4 (E3))

Preparation of 3-fluoro-4-(1-butylpentyloxycarbonyl)phenyl=4'-n-nonyloxybiphenyl-4-carboxylate The end-products were obtained in the same manner as in Example 1 except that 3-pentanol was replaced with 4-heptanol (Example 2) or 5-nonanol (Example 3).

Comparative Example 1 (Formula (1): A=—O—, m=9, (n) =—CH$_2$CH(C$_2$H$_5$)$_2$ (CE1))

Preparation of 3-fluoro-4-(2-ethylbutyloxycarbonyl)phenyl=4'-n-nonyloxybiphenyl-4-carboxylate (CE1)

The end product was obtained in the same manner as in Example 1 except that 3-pentanol was replaced with 2-ethyl-1-butanol.

Comparative Example 2 (Formula (1): A=—O—, m=9, (n) =—CH$_2$CH(C$_3$H$_7$)$_2$ (CE2))

Preparation of 3-fluoro-4-(2-propylpentyloxycarbonyl)phenyl=4'-n-nonyloxybiphenyl-4-carboxylate (CE2)

The end product was obtained in the same manner as in Example 1 except that 3-pentanol was replaced with 2-propyl-1-pentanol.

Example 4 (Formula (1): A=—O—, m=6, n=2 (E4))

Preparation of 3-fluoro-4-(1-ethylpropyloxycarbonyl)phenyl=4'-n-hexyloxybiphenyl-4-carboxylate Example 5 (Formula (1): A=—O—, m=8, n=2 (E5))

Preparation of 3-fluoro-4-(1-ethylpropyloxycarbonyl)phenyl=4'-n-octyloxybiphenyl-4-carboxylate Example6 (Formula (1): A=—O—, m=10, n=2 (E6))

Preparation of 3-fluoro-4-(1-ethylpropyloxycarbonyl)phenyl=4'-n-decyloxybiphenyl-4-carboxylate The end products were obtained in the same manner as in Example 1 except that n-nonyl bromide was replaced with n-hexyl bromide (Example 4), n-octyl bromide (Example 5) or n-decyl bromide (Example 6).

Example 7 (Formula (1): A=—O—, m=6, n=3 (E7))

Preparation of 3-fluoro-4-(1-propylbutyloxycarbonyl)phenyl=4'-n-hexyloxybiphenyl-4-carboxylate Example 8 (Formula (1): A=—O—, m=8, n=3 (E8))

Preparation of 3-fluoro-4-(1-propylbutyloxycarbonyl)phenyl=4'-n-octyloxybiphenyl-4-carboxylate Example 9 (Formula (1): A=—O—, m=10, n 3 (E9))

Preparation of 3-fluoro-4-(1-propylbutyloxycarbonyl)phenyl=4'-n-decyloxybiphenyl-4-carboxylate The end products were obtained in the same manner as in Example 1 except that n-nonyl bromide was replaced with n-hexyl bromide (Example 7), n-octyl bromide (Example 8) or n-decyl bromide (Example 9) and that 3-pentanol was replaced with 4-heptanol in each Example.

Example 10 (Formula (1): A=single bond (—), m=9, n=3 (E10))

Preparation of 3-fluoro-4-(1-propylbutyloxycarbonyl)phenyl=4'-n-nonylbiphenyl-4-carboxylate The end product was obtained in the same manner as in Example 1 except that 4-(4'-n-nonyl) biphenylcarboxylic acid prepared below was used.

(1) Preparation of 4-(4'-n-nonyl)biphenylcarboxylic acid

A stirrer, a thermometer, a dropping funnel and a condenser were attached to a 1-liter four-necked flask. The flask was charged with 0.192 mol of biphenyl and 0.192 mol of aluminum chloride pulverized in advance, and 120 ml of carbon disulfide was added thereto. After 0.192 mol of octanoyl chloride was added dropwise through the dropping funnel at room temperature over about 1 hour, the mixture was further stirred at room temperature for 3 hours.

The reaction mixture was poured into a mixture comprising 8 ml of concentrated hydrochloric acid and ice water, and the resulting mixture was extracted with dichloromethane. Thereafter, an extract was washed with water and then dried over anhydrous sodium sulfate.

The solvent was distilled off to give 62.2 g of a crude product. The crude product was recrystallized from ethanol to give 50 g of octyl biphenyl ketone.

A stirrer, a thermometer and a reflux condenser were attached to a 1-liter four-necked flask. The flask was charged with 0.147 mol of the above-obtained octyl biphenyl ketone, 0.521 mol of sodium hydroxide, 0.517 mol of hydrazine monohydrate and 300 ml of triethylene glycol, and the mixture was heated at 160° C. for 1 hour with stirring to distill off water being formed.

Then, the reaction mixture was continuously stirred under heating at 200° C. for 2 hours.

After allowed to cool, the reaction mixture was poured into water and then extracted with toluene. An extract was washed with water, and the solvent was then distilled off to give 47.6 g of a crude product.

The crude product was purified with a silica gel column using hexane as a solvent to give 34.5 g of nonyl biphenyl.

A stirrer, a thermometer, a dropping funnel and a condenser were attached to a 1-liter four-necked flask. The flask was charged with 0.107 mol of the above-obtained nonyl biphenyl, 0.111 mol of pulverized aluminum chloride and 110 ml of carbon disulfide.

The reactor was cooled, and 0.109 mol of oxalic acid chloride was added dropwise through the dropping funnel so as to reach a temperature of 10° C. or lower. After the addition, the mixture was further stirred at room temperature for 2 hours.

The reaction mixture was poured into ice water and then extracted with dichloromethane. The solvent was then distilled off. To this were added 400 ml of tetrahydrofuran, 12 g of sodium hydroxide and 100 ml of water, and the mixture was refluxed under heating for 1 hour to be hydrolyzed.

After allowed to cool, the reaction mixture was poured into water, and concentrated hydrochloric acid was added to acidify the mixture.

A precipitated solid was recovered by filtration and air-dried to give about 40 g of a crude product. The crude product was recrystallized from toluene to give 17.5 g of the end product.

Example 11 (Formula (1): A=—COO—, m=9, n=3 (E11))

Preparation of 3-fluoro-4-(1-propylbutyloxycarbonyl)phenyl=4'-n-decanoyloxybiphenyl-4-carboxylate The end product was obtained in the same manner as in Example 1 except that 4-(4'-n-decanoyloxy) biphenylcarboxylic acid prepared below was used.

(1) Preparation of 4-(4'-n-decanoyloxy) biphenylcarboxylic acid 10.0 Grams of 4-(4'-hydroxy)biphenylcarboxylic acid, 9.8 g of n-decanoic acid chloride, 16 ml(milliliter) of triethylamine and 1 g of dimethylaminopyridine were dissolved in 150 ml of dichloromethane, and the mixture was stirred at room temperature for one day.

After the completion of the reaction, 50 ml of 10% hydrochloric acid was added, and the mixture was extracted with 100 ml of ether three times. An organic layer was washed with 100 ml of sodium chloride aqueous solution three times and then dried over anhydrous sodium sulfate.

The solvent was distilled off, and a remainder was washed with 400 ml of hexane to give the end product.

The formulae of the compounds (E1 to E-11) obtained in Examples 1 to 11 and the compounds (CE1 and CE2) obtained in Comparative Examples 1 and 2 are shown below. Table 1 shows $^1$H-NMR spectrum data of these compounds.

Table 2 also shows the results of identifying liquid crystal phases. The liquid crystal phases were identified by texture observation and measurement with a DSC (differential scanning calorimeter).

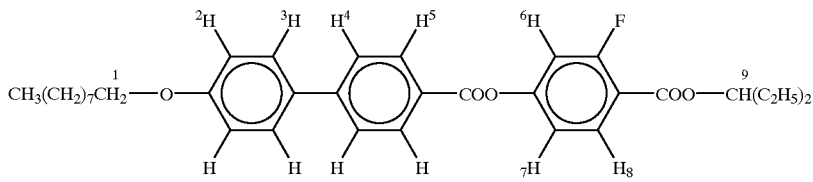
(E1)

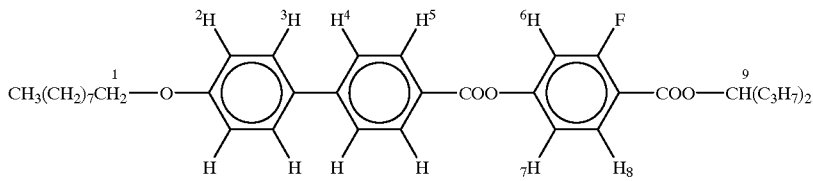
(E2)

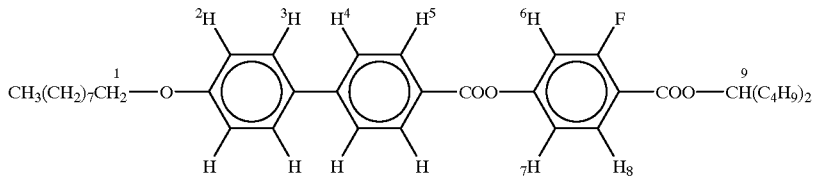
(E3)

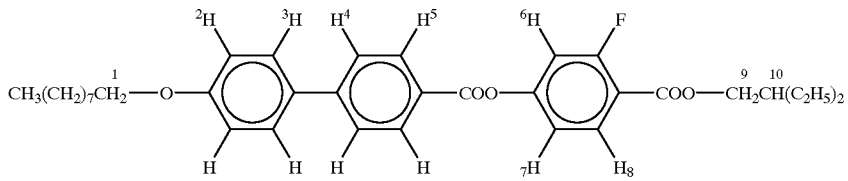
(CE1)

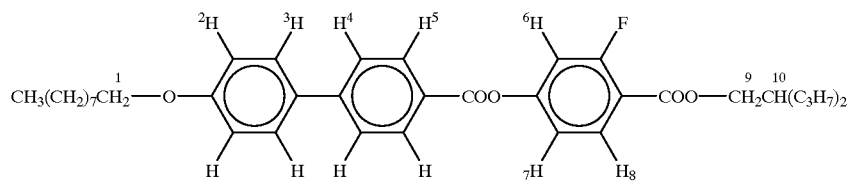
(CE2)
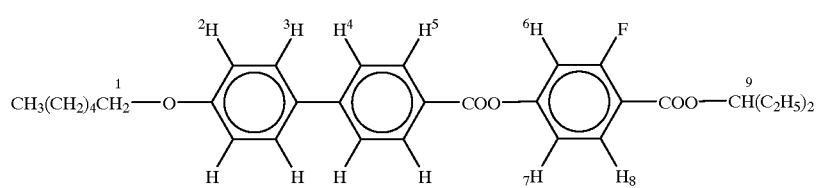
(E4)
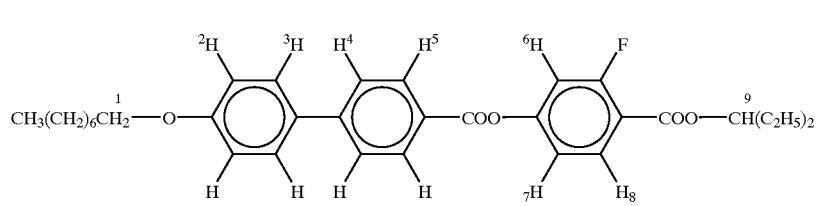
(E5)
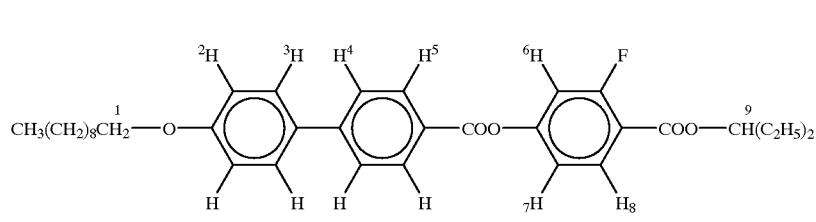
(E6)
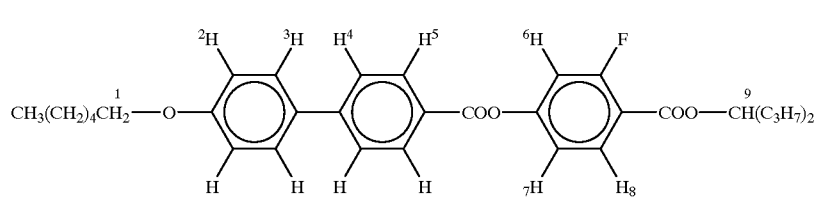
(E7)
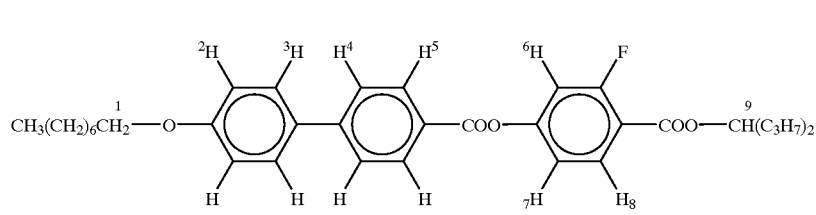
(E8)
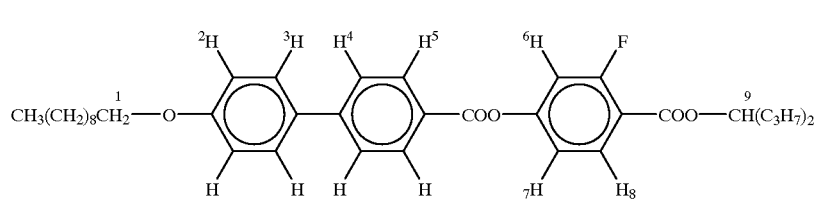
(E9)
(E10)

-continued

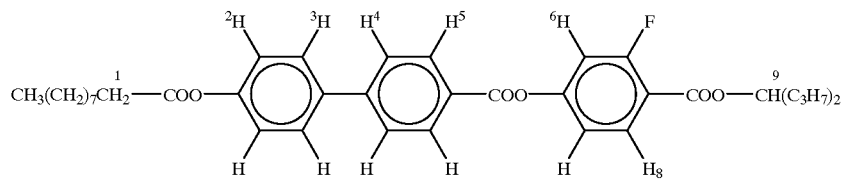
(E11)

TABLE 1

| | Chemical shift (ppm) | | | | | | | | |
| --- | --- | --- | --- | --- | --- | --- | --- | --- | --- |
| | 1 H | 2 H | 3 H | 4 H | 5 H | 6 H | 7 H | 8 H | 9 H | 10 H |
| Ex. 1 | 4.0 | 7.0 | 7.6 | 7.7 | 8.2 | 7.1 | 7.1 | 8.0 | 5.0 | |
| Ex. 2–3 | 4.0 | 7.0 | 7.6 | 7.7 | 8.2 | 7.1 | 7.1 | 8.0 | 5.2 | |
| C. Ex. 1 | 4.0 | 7.0 | 7.6 | 7.7 | 8.2 | 7.1 | 7.1 | 8.0 | 4.3 | 1.2–1.6 |
| C. Ex. 2 | 4.0 | 7.0 | 7.6 | 7.7 | 8.2 | 7.1 | 7.1 | 8.0 | 4.3 | 1.8 |
| Ex. 4–9 | 4.0 | 7.0 | 7.6 | 7.7 | 8.2 | 7.1 | 7.1 | 8.0 | 5.0 | |
| Ex. 10 | 2.6 | 7.3 | 7.6 | 7.7 | 8.3 | 7.1 | | 8.0 | 5.2 | |
| Ex. 11 | 2.6 | 7.3 | 7.6 | 7.7 | 8.3 | 7.1 | | 8.0 | 5.2 | |

Ex.: Example
C. Ex.: Comparative Example

TABLE 2

| | Phase sequence | Melting point |
| --- | --- | --- |
| Ex. 1 | I(142)SA(122)SCA'(-2)SX(-29)SY(<-30)Cr | 60° C. |
| Ex. 2 | I(105)SA(98)SCA'(3)SX(<0)Cr | 62° C. |
| Ex. 3 | I(86)SA(80)SCA'(-32)SX(<-40)Cr | 73° C. |
| C. Ex. 1 | I(156)SA(136)SC'(10)SX(-27)Cr | 51° C. |
| C. Ex. 2 | I(130)SA(115)SC'(<0)Cr | 69° C. |
| Ex. 4 | I(157)SA(124)SCA'(41)SX(33)SY(<-30)Cr | 63° C. |
| Ex. 5 | I(146)SA(124)SCA'(17)SX(-15)SY(<-30)Cr | 62° C. |
| Ex. 6 | I(140)SA(119)SC'(116)SCA'(-26)SX(<-29)SY(<-30)Cr | unknown |
| Ex. 7 | I(131)SA(117)SCA'(51)SX(39)SY(17)SZ(<-30)Cr | 58° C. |
| Ex. 8 | I(112)SA(106)SCA'(<-30)Cr | 78° C. |
| Ex. 9 | I(100)SA(95)SCA'(-20)SX(<-30)Cr | 37° C. |
| Ex. 10 | I(62)SA(58)SCA'(-21)Cr | 46° C. |
| Ex. 11 | I(112)SA(101)SCA'(29)Cr | 46° C. |

Ex.: Example
C. Ex.: Comparative Example
Note:
In Table 2, parenthesized value shows a phase transition temperature (° C.), I is an isotropic phase, SA is a smectic A phase, SCA' is an achiral anti-ferroelectric phase, SC' is an achiral ferroelectric phase, SX, SY and SZ are unidentified liquid crystal phases, and Cr is a crystal phase.

What is claimed is:

1. A swallow=tail-shaped liquid crystal compound of the following general formula (1),

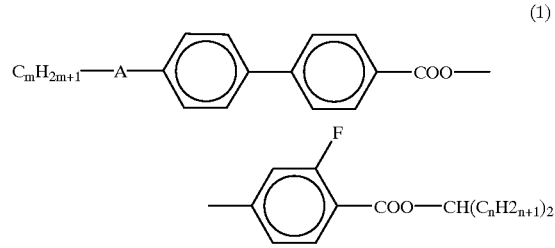
(1)

wherein a is —O—, —COO— or a single bond (—), m is an integer of 4 to 12, and n is an integer of 2 to 4.

2. The compound of claim 1, wherein m in the general formula (1) is 6 to 10.

3. The compound of claim 1, wherein n in the general formula (1) is an integer of 2 or 3.

4. The compound of claim 1, which has an achiral anti-ferroelectric phase whose lower limit temperature is lower than or equal to room temperature and whose upper limit temperature is higher than or equal to 50° C.

* * * * *